US006443962B1

(12) United States Patent
Gaber (10) Patent No.: US 6,443,962 B1
(45) Date of Patent: Sep. 3, 2002

(54) STITCHING TOOL (75) Inventor: Benny Gaber, Motskin Street 20 P.O. Box 2033, Tirat Hacarmel (IL), 39120

(73) Assignee: Benny Gaber (IL)

( * ) Notice: Subject to any disclaimer, the term of this patent is extended or adjusted under 35 U.S.C. 154(b) by 0 days.

(21) Appl. No.: 09/523,150

(22) Filed: Mar. 10, 2000

(51) Int. Cl.[7] .............................................. A61B 17/04
(52) U.S. Cl. ...................... 606/144; 606/139; 112/80.04
(58) Field of Search ................. 606/139, 144, 606/148; 112/80.03, 80.04, 169

(56) References Cited

U.S. PATENT DOCUMENTS

| 4,557,265 A | * 12/1985 | Andersson ................. 606/144 |
| 5,306,281 A | 4/1994 | Beurrier ..................... 606/144 |
| 5,364,408 A | 11/1994 | Gordon ....................... 606/144 |
| 5,458,609 A | 10/1995 | Gordon et al. .............. 606/144 |
| 5,540,704 A | 7/1996 | Gordon et al. .............. 606/144 |
| 5,575,800 A | 11/1996 | Gordon ....................... 606/144 |
| 5,578,044 A | 11/1996 | Gordon et al. .............. 606/144 |
| 5,709,693 A | 1/1998 | Taylor ........................ 606/145 |

FOREIGN PATENT DOCUMENTS

WO    WO 97 29694 A    8/1997

OTHER PUBLICATIONS

Endo Stitch® Catalogue, United States Surgical Corp., Norwalk, CT, USA.

* cited by examiner

*Primary Examiner*—David O. Reip
*Assistant Examiner*—Julian W. Woo
(74) *Attorney, Agent, or Firm*—Pennie & Edmonds LLP

(57) ABSTRACT

A stitching tool including a needle including an arcuate shank having an arcuate length extending from a needle point at one end thereof to another end, called a suture end, and wherein the needle is toothed along at least a portion of the length.

4 Claims, 11 Drawing Sheets

STITCHING TOOL

FIELD OF THE INVENTION

The present invention relates generally to a stitching tool useful for tying tissues with sutures, typically in endoscopic surgery.

BACKGROUND OF THE INVENTION

Stitching tools for tying tissues with sutures in endoscopic surgery are well known. U.S. Pat. Nos. 5,364,408; 5,458,609; 5,540,704; 5,575,800 and 5,578,044, all assigned to Laurus Medical Corp., Irvine, Calif., USA, are drawn to a family of suturing systems and needle drivers marketed under the name Push & Catch™. The needle driver automatically captures and retrieves sutures for tying sutures in tissues.

A disposable suturing device marketed under the trademark Endo Stitch® by United States Surgical Corp., Norwalk, Conn., USA, is another known device for tying sutures in tissues in endoscopic surgery.

SUMMARY OF THE INVENTION

The present invention seeks to provide a stitching tool useful for suturing and ligation of tissues in endoscopic procedures, such as Burch urethropexy, oophorectomy, cholecystectomy, myomectomy, hysterectomy, trocal wound closure and paravaginal repair.

There is thus provided in accordance with a preferred embodiment of the present invention a stitching tool including a needle including an arcuate shank having an arcuate length extending from a needle point at one end thereof to another end, called a suture end, and wherein the needle is toothed along at least a portion of the length.

In accordance with a preferred embodiment of the present invention the suture end is adapted for attachment thereto of a suture.

Further in accordance with a preferred embodiment of the present invention the arcuate shank defines a curve having at least one focus and the needle is toothed along a surface furthest from the at least one focus.

Additionally in accordance with a preferred embodiment of the present invention the stitching tool includes a needle manipulator including a housing with an arcuate channel formed therein through which moves the needle, the channel defining an arc extending from a first end to a second end, wherein as the needle moves through the channel, the needle point exits the housing at the first end and re-enters the housing at the second end and the arc is sufficiently long such that at least one of the needle point and the suture end is always in the channel during moving of the needle. The stitching tool also preferably includes an actuator for moving the needle through the channel. Preferably the actuator is coupled to the needle by a toothed belt which meshes with the toothed needle.

Preferably the arcuate channel defines a curve having at least one focus and the needle is rotatable about the focus at least 360°.

Instead of the needle being toothed, a standard, smooth arcuate needle may be employed as well. The actuator may move the needle by means of a belt snugly fit between the needle and the arcuate channel. The surface of the belt which contacts the needle has a higher coefficient of friction than the surface of the belt which contacts the channel. The belt presses against the needle and as the actuator moves the belt, the belt moves the needle by means of friction through the channel.

There is also provided in accordance with a preferred embodiment of the present invention a stitching tool including a needle including an arcuate shank having an arcuate length extending from a needle point at one end thereof to another end, called a suture end, and a needle manipulator including a housing with an arcuate channel formed therein through which moves the needle, the channel defining an arc extending from a first end to a second end, wherein as the needle moves through the channel, the needle point exits the housing at the first end and re-enters the housing at the second end and the arc is sufficiently long such that at least one of the needle point and the suture end is always in the channel during moving of the needle.

Additionally in accordance with a preferred embodiment of the present invention the arcuate channel is bounded by a disc, which rotates about the at least one shank focus, and an upper housing portion. The disc has an axle disposed in an enlarged hole so that the axle can translate within the boundary of the enlarged hole, and the disc can rotate eccentrically about the at least one shank focus.

In accordance with a preferred embodiment of the present invention the disc includes a rim with a surface that is contactable with the needle and the upper housing portion includes a surface that is contactable with the needle, wherein the rim contacting surface has a higher frictional contact with the needle than the upper housing portion contacting surface.

The disc may be pulled (because of the axle being in the enlarged hole) so that the rim of the disc presses the needle against the upper housing portion. Once the needle is pinched between the disc and the upper housing portion, rotation of the disc causes rotation of the needle due to the difference in coefficient of friction between the needle/rim contact and the needle/housing contact.

Further in accordance with a preferred embodiment of the present invention the stitching tool includes a link eccentrically attached to the disc, wherein pulling of the link in a direction away from a centerline of the disc causes the disc to impart an advancing angular movement to the needle. Pulling the link first pinches the needle between the disc and the upper housing portion and further pulling of the link, due to its eccentric mounting to the disc, causes the disc and the needle to rotate about the at least one shank focus.

Still further in accordance with a preferred embodiment of the present invention the disc includes a first half and a second half, and a link is attached to the first half, wherein pulling of the link in a direction away from a centerline of the disc causes the first half of the disc to impart an advancing angular movement to the needle and pushing the link in a direction towards the centerline causes the second half of the disc to press against the needle and to prevent regressive angular movement of the needle opposite to the advancing angular movement.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
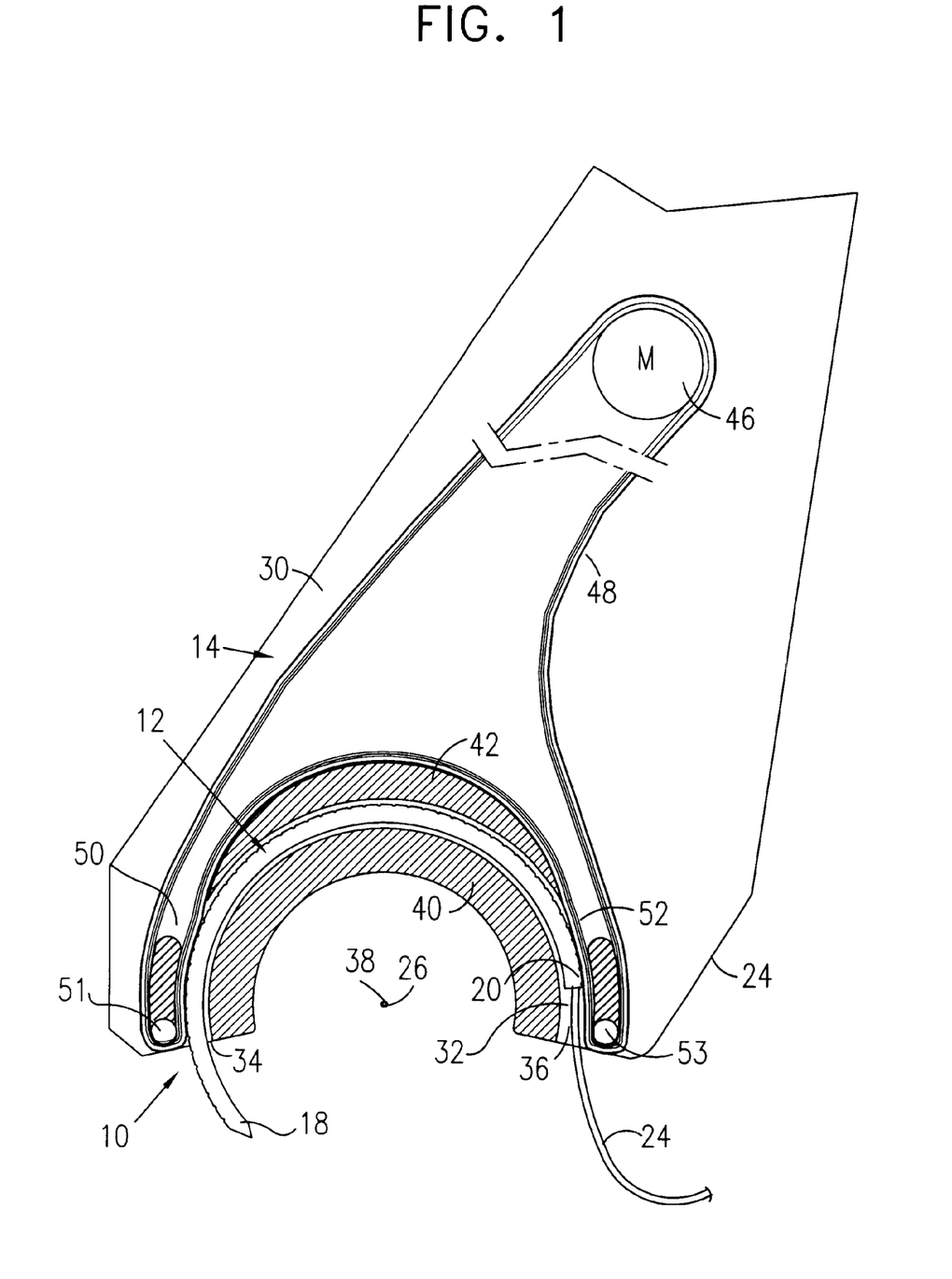
FIG. 1 is a simplified pictorial illustration of a stitching tool constructed and operative in accordance with a preferred embodiment of the present invention.

Reference is now made to FIG. 1 which illustrates a stitching tool 10 constructed and operative in accordance with a preferred embodiment of the present invention.

Figure 2A:
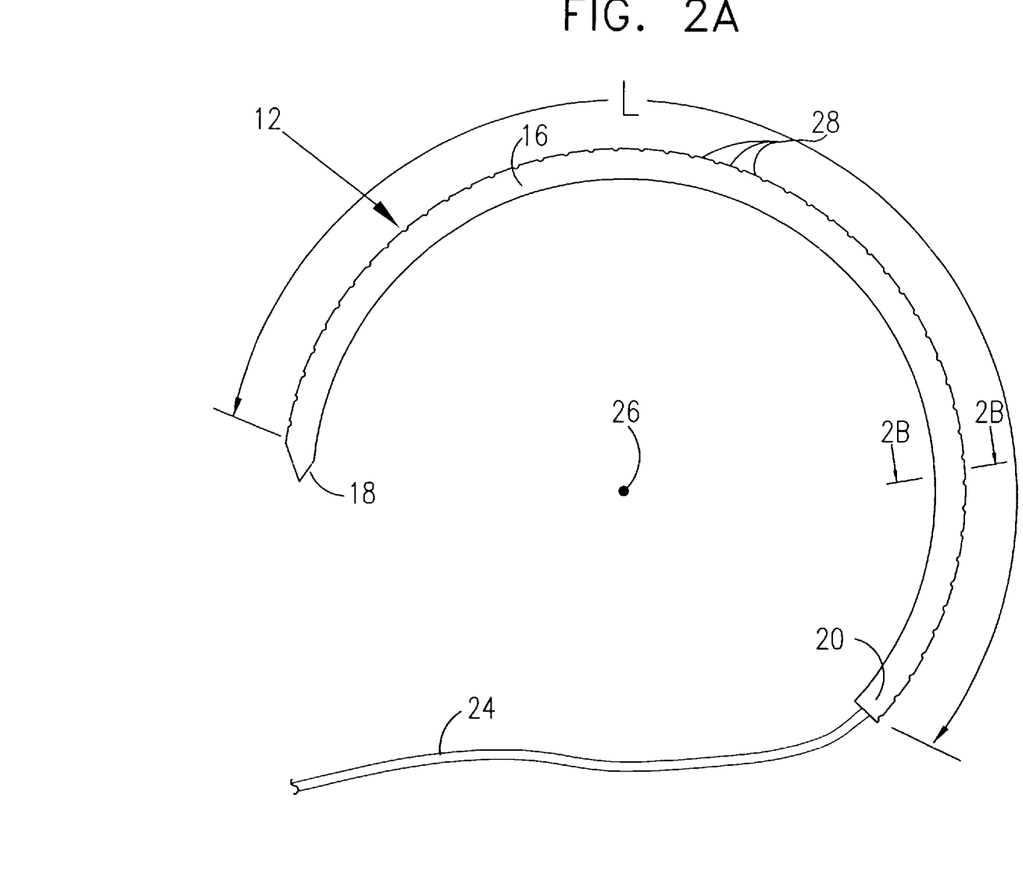
FIG. 2A is a simplified pictorial illustration of a needle with an arcuate shank, constructed and operative in accordance with a preferred embodiment of the present invention, and useful in the stitching tool of FIG. 1.

Stitching tool 10 includes a needle 12, illustrated in greater detail in FIG. 2A, disposed in a needle manipulator 14. Referring to FIG. 2A, it is seen that needle 12 preferably includes an arcuate shank 16 having an arcuate length L extending from a needle point 18 at one end thereof to another end, called a suture end 20. Length L preferably subtends an arc greater than 180°. The diameter, shape and length of needle 12 are in accordance with the particular application. Needle 12 is preferably constructed of a medically safe and durable material, such as austenitic stainless steel 316L. In accordance with a preferred embodiment of the present invention, needle 12 is toothed along at least a portion of its length. By "toothed" it is meant that one or more teeth 22 are formed along the length of needle 12. Alternatively, instead of protrusions such as teeth, the term "toothed" also encompasses dimples, grooves, recesses or pits that can be meshed with a correspondingly formed drive member, such as a timing belt. Teeth 22 may have any tooth profile and any pitch. Preferably suture end 20 is adapted for attachment thereto of a suture 24, although alternatively suture 24 may be attached anywhere else along shank 16.

It is noted that throughout the specification and the claims, the term "suture" encompasses any suture, thread, filament or wire suitable for stitching, sewing or ligating.

Figure 2B:
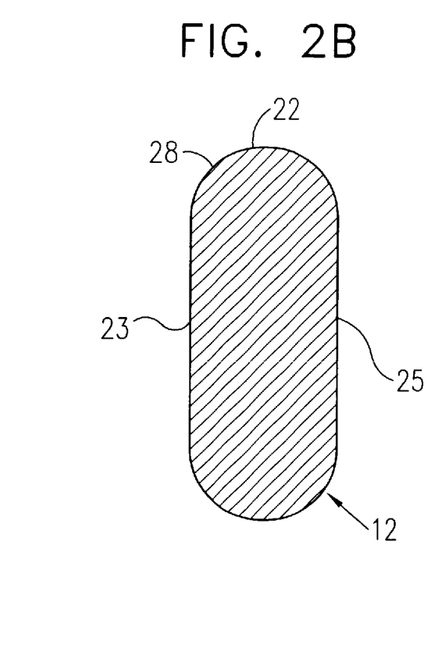
FIG. 2B is a simplified sectional illustration of the needle of FIG. 2A, taken along lines 2B—2B in FIG. 2A.

Preferably arcuate shank 16 defines a curve having at least one focus 26. Most preferably the curve is a circle and focus 26 is the center of the circle. Preferably needle 12 is toothed along a surface 28 furthest from focus 26. Referring to FIG. 2B, it is seen that needle 12 preferably has two flattened surfaces 23 and 25 generally along the sides of surface 28.

Referring again to FIG. 1, it is seen that needle manipulator 14 preferably includes a housing 30 with an arcuate channel 32 formed therein through which moves needle 12. Housing 30 may be constructed of any suitable material, such as a plastic. Channel 32 defines an arc extending from a first end 34 to a second end 36 and also defines a curve having at least one focus 38. Most preferably the curve of channel 32 is a circle and focus 38 is the center of the circle. Most preferably foci 26 and 38 coincide or nearly coincide. Needle 12 is rotatable about focus 38 at least 360°, and is most preferably continuously rotatable about focus 38. As needle 12 moves through channel 32, needle point 18 exits housing 30 at first end 34 and re-enters housing 30 at second end 36. The arc of channel 32 is sufficiently long such that at least one of needle point 18 and suture end 20 is always in channel 32 during moving of needle 12. Needle 12 may be initially inserted into channel 32 in any convenient manner, such as by removing a removable cover (not shown) provided over channel 32.

Figure 3:
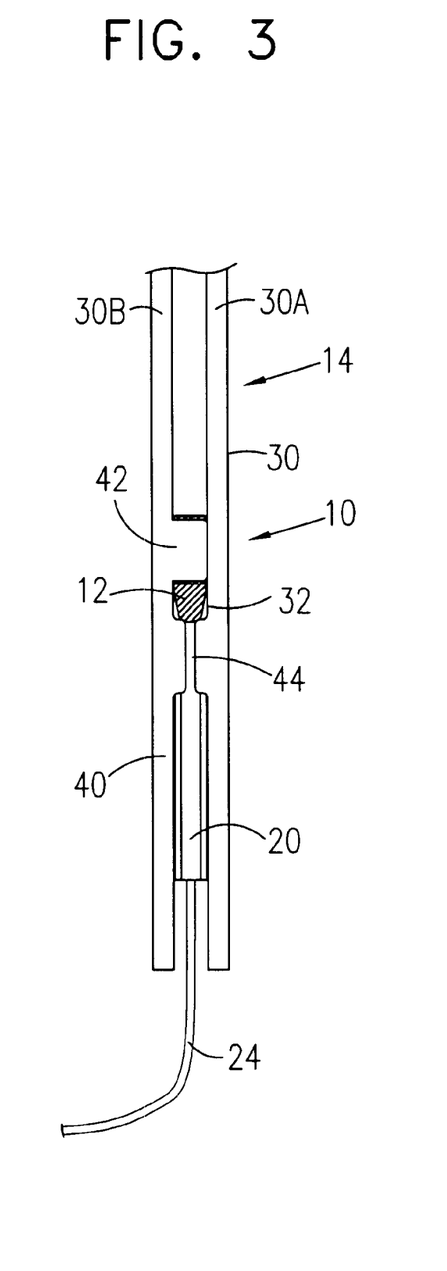
FIG. 3 is a simplified side view illustration of the stitching tool of FIG. 1.

Reference is now additionally made to FIG. 3 which is a side view illustration of a portion of stitching tool 10. It is seen that housing 30 is preferably constructed of two halves 30A and 30B, joined together by any means, such as bonding, welding or fasteners. Channel 32 is preferably bounded by a lower housing portion 40 and an upper housing portion 42. Preferably housing halves 30A and 30B form a gap 44 leading from channel 32 to lower housing portion 40, gap 44 being of sufficient width for suture 24 to pass therethrough.

Referring again to FIG. 1, an actuator 46, such as a motor, is preferably provided for moving needle 12 through channel 32. Preferably actuator 46 is coupled to needle 12 by a toothed belt 48 which meshes with teeth 22 of needle 12. Belt 48 is constantly in operatively meshed contact with needle 12 at two locations 50 and 52, respectively near first end 34 and second end 36. Static or roller guides 51 and 53 may be provided for guiding the travel of belt 48. It is appreciated that, less preferably, instead of actuator 46 and belt 48, two gear motors could be directly operatively meshed with needle 12 at locations 50 and 52. A suitable power source (not shown) such as a battery is provided for powering actuator 46.

Figure 4A:
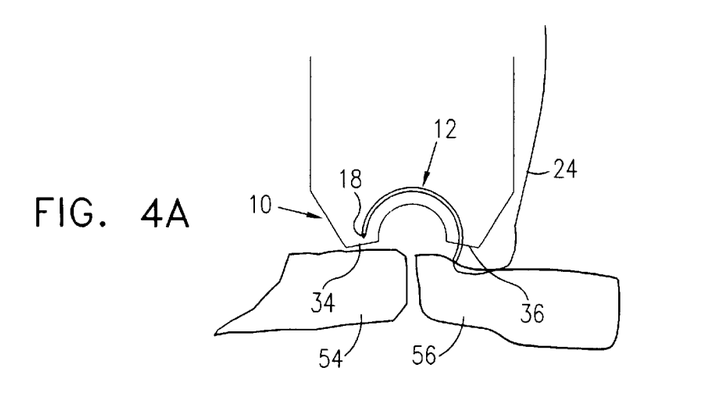
FIGS. 4A–4H are simplified illustrations of stitching two tissues together with the stitching tool of FIG. 1 in accordance with a preferred embodiment of the present invention.

Reference is now made to FIGS. 4A–4H which illustrate stitching two tissues 54 and 56 together with stitching tool 10 in accordance with a preferred embodiment of the present invention. In FIG. 4A, first end 34 and second end 36 are placed against tissues 54 and 56. Initially, needle point 18 is flush with first end 34.

Figure 4B:
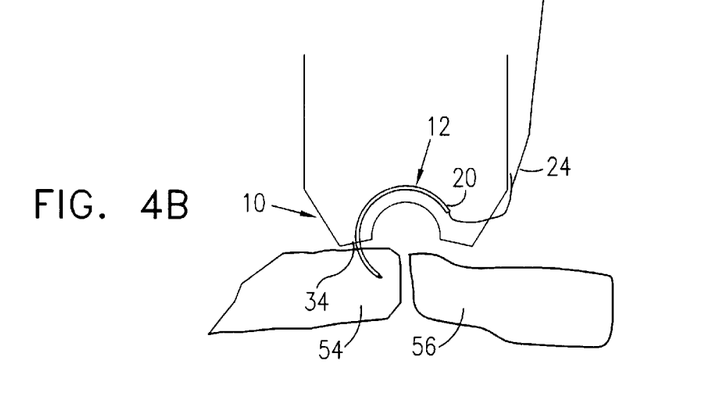
Figure 4C:
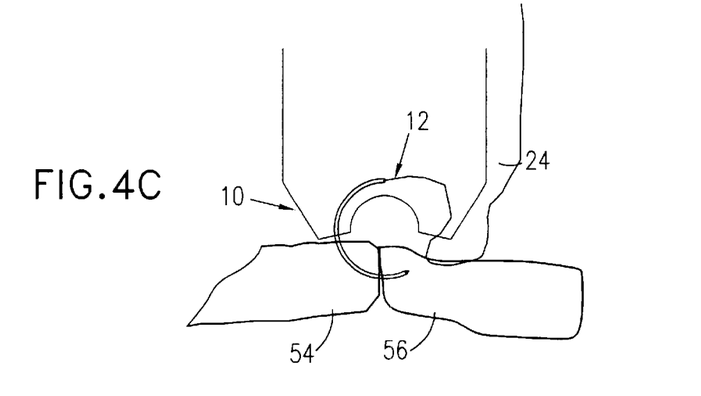

In FIG. 4B, actuator 46 (not shown) rotates needle 12 counterclockwise in the sense of FIG. 4B. Needle 12 exits first end 34 and pierces tissue 54. Suture 24 trails after suture end 20 into channel 32. In FIG. 4C, upon further rotation, needle 12 continues through tissue 54 and pierces tissue 56.

Figure 4D:
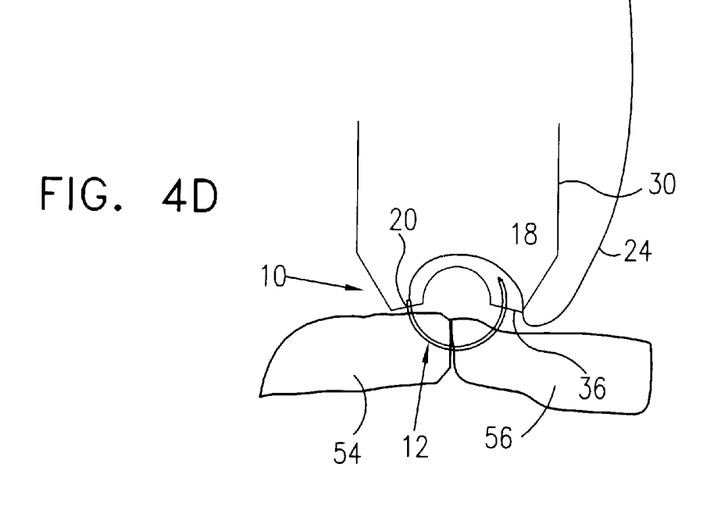
Figure 4E:
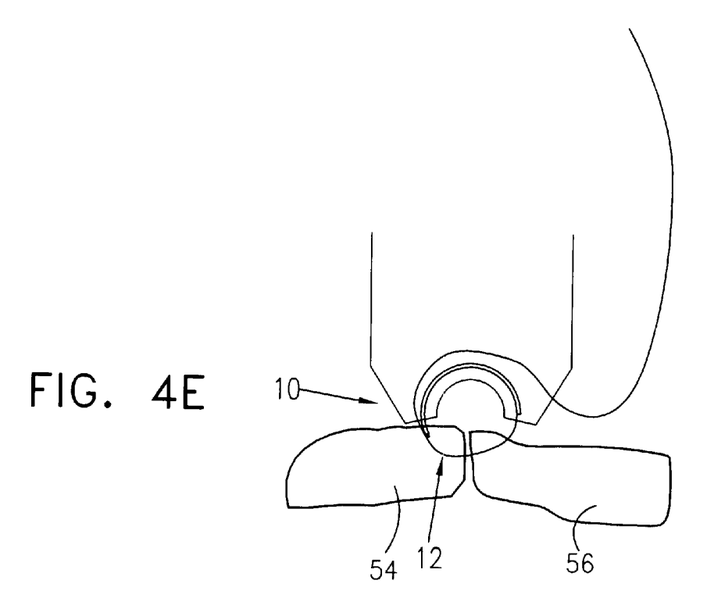

In FIG. 4D, upon further rotation, needle 12 passes completely through tissue 56 and re-enters housing 30 at second end 36. At this point, needle 12 has been rotated over 180°. As mentioned above, it is seen that the arc of channel 32 is sufficiently long such that needle point 18 and suture end 20 are always in channel 32 during moving of needle 12. In FIG. 4E, needle 12 has been rotated about 360° and suture 24 has been drawn through both tissues 54 and 56.

Figure 4F:
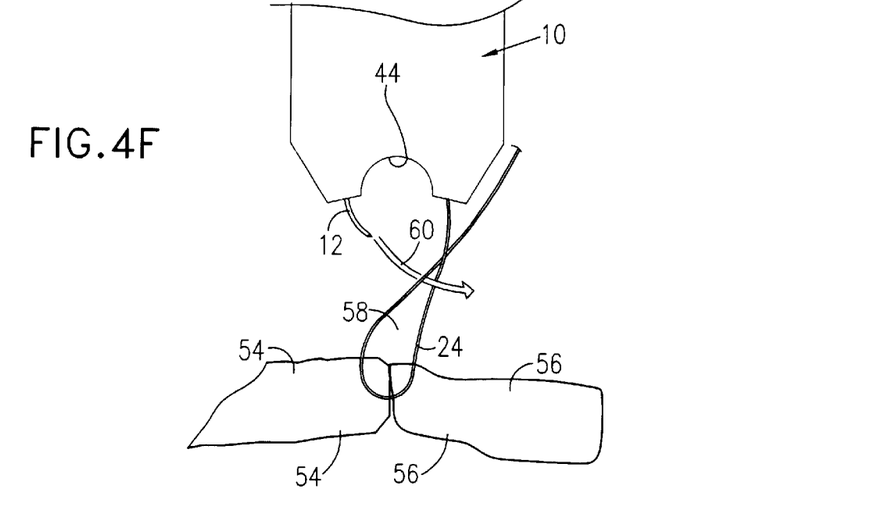
Figure 4G:
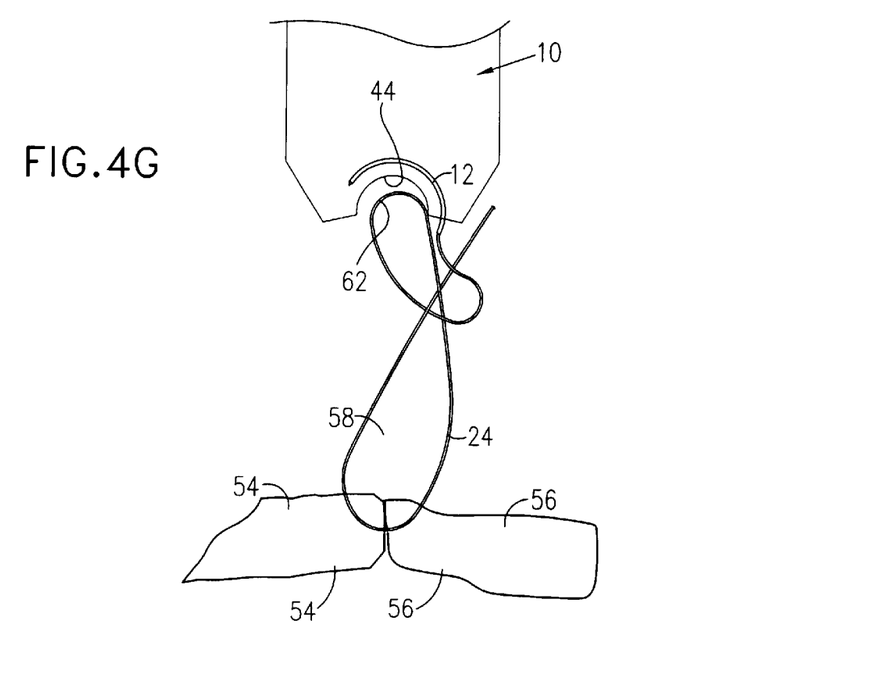
Figure 4H:
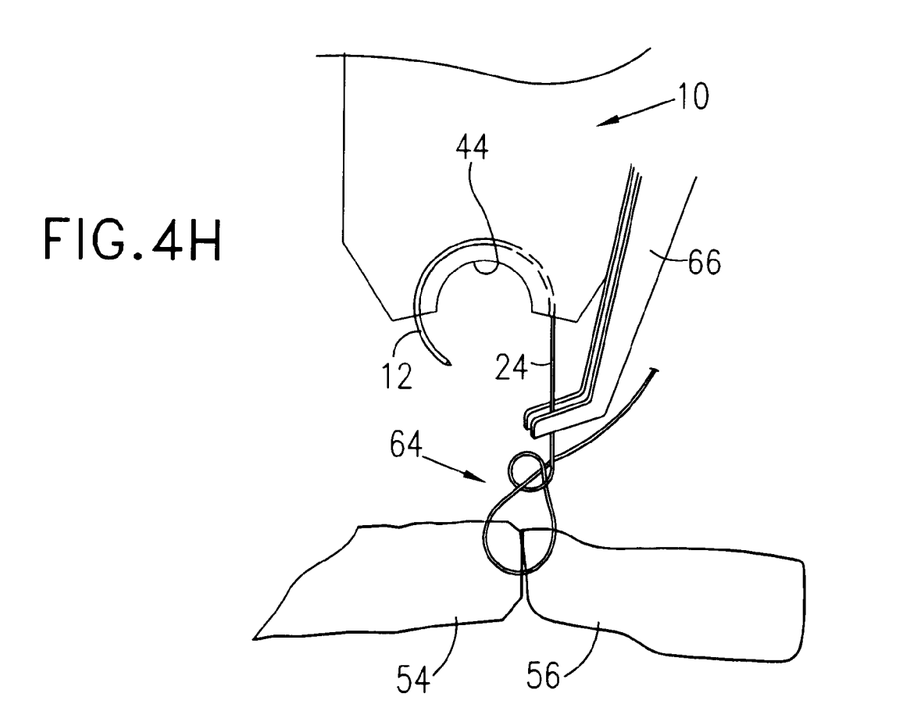

In FIG. 4F, stitching tool 10 is pulled away from the tissues, thereby creating a loop 58. It is noted that suture 24 has dropped through gap 44 (FIG. 3) in order to form loop 58. Needle 12 is then further rotated and passed through loop 58 generally in the direction of an arrow 60. In FIG. 4G, needle 12 re-enters housing 30 at second end 36 and a portion of suture 24 designated by reference numeral 62 starts to drop through gap 44. In FIG. 4H, stitching tool 10 is pulled away from tissues 54 and 56 thereby creating a knot 64. Stitching tool 10 is pulled away from the tissues a distance that provides an adequate length of extra suture for tying further knots in the tissues adjacent to knot 64. After having provided this extra length of suture 24, knot 64 may be tightened by pushing against knot 64 with a knot pusher 66 and simultaneously keeping the extra length of suture 24 taught with stitching tool 10. Knot pusher 66 may be attached to stitching tool 10, or alternatively, may be separate from stitching tool 10.

Figure 5:
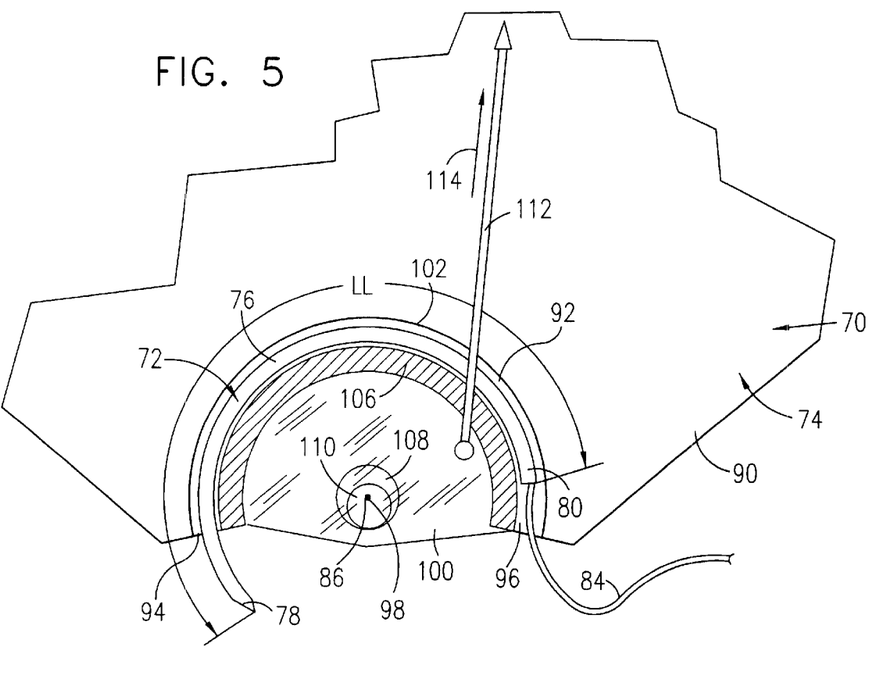
FIG. 5 is a simplified pictorial illustration of a stitching tool constructed and operative in accordance with another preferred embodiment of the present invention.

Reference is now made to FIG. 5 which illustrates a stitching tool 70 constructed and operative in accordance with another preferred embodiment of the present invention.

Stitching tool 70 includes a needle 72 disposed in a needle manipulator 74. Needle 72 preferably includes an arcuate shank 76 having an arcuate length LL extending from a needle point 78 at one end thereof to another end, called a suture end 80. Needle 72 is preferably similar in construction to needle 12, except that needle 72 does not have any teeth. Preferably suture end 80 is adapted for attachment thereto of a suture 84, although alternatively suture 84 may be attached anywhere else along shank 76. Preferably arcuate shank 76 defines a curve having at least one focus 86. Most preferably the curve is a circle and focus 86 is the center of the circle.

Needle manipulator 74 preferably includes a housing 90 with an arcuate channel 92 formed therein through which moves needle 72. Housing 90 may be constructed of any suitable material, such as a plastic. Channel 92 defines an arc extending from a first end 94 to a second end 96 and also defines a curve having at least one focus 98. Most preferably the curve of channel 92 is a circle and focus 98 is the center of the circle. Most preferably foci 86 and 98 coincide or nearly coincide. Needle 72 is rotatable about focus 98 at least 360°, and is most preferably continuously rotatable about focus 98. As needle 72 moves through channel 92, needle point 78 exits housing 90 at first end 94 and re-enters housing 90 at second end 96. The arc of channel 92 is sufficiently long such that at least one of needle point 78 and suture end 80 is always in channel 92 during moving of needle 72.

Channel 92 is preferably bounded by a disc 100 and a low friction upper housing portion 102. Disc 100 comprises a rim 106, preferably made of a high friction material, such as a roughened plastic. Housing 90 is formed with a hole 108 centered at focus 98 and through which passes an undersized axle 110. Thus disc 100 is arranged to rotate eccentrically about axle 110. Needle 72 passes through channel 92 between the high friction rim 106 and low friction upper housing portion 102, needle 72 itself being preferably smooth.

Figure 6:
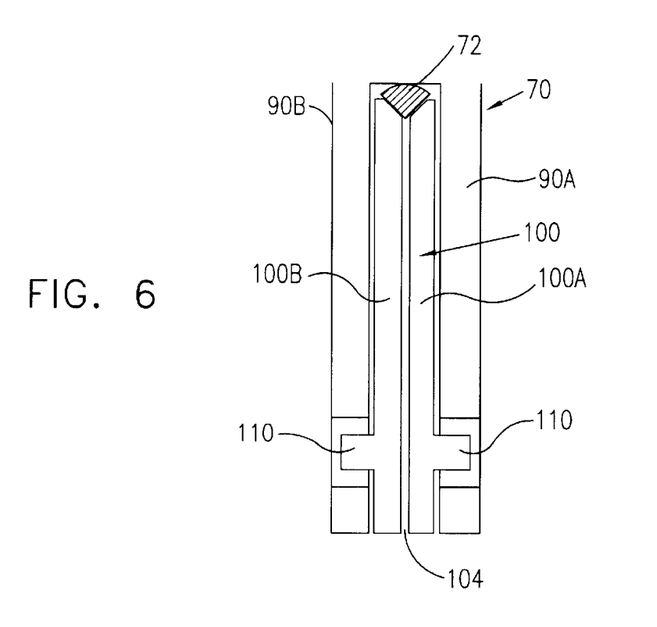
FIG. 6 is a simplified side view illustration of the stitching tool of FIG. 5.

Reference is now additionally made to FIG. 6 which is a side view illustration of a portion of stitching tool 70. It is seen that disc 100 is preferably constructed of two halves 100A and 100B. Preferably disc halves 100A and 100B define a gap 104 of sufficient width for suture 84 to pass therethrough. Housing, 90 is preferably constructed of two halves 90A and 90B, one of the halves possibly serving as a removable cover for initial insertion of needle 72.

A link 112 is preferably attached to disc 100 at disc half 100A. Link 112 can pull disc half 100A generally in the direction of an arrow 114, thereby pressing disc 100 against needle 72 and causing needle 72 to move through channel 92 as is now described with reference to FIGS. 7A–7C. Link 112 is stiff so that it can also push disc half 100A in the direction of an arrow 115, opposite to the direction of arrow 114. Link 112 may be manually pulled/pushed or alternatively be manipulated by a suitable automatic device, such as a solenoid or actuator, preferably a motor.

Figure 7A:
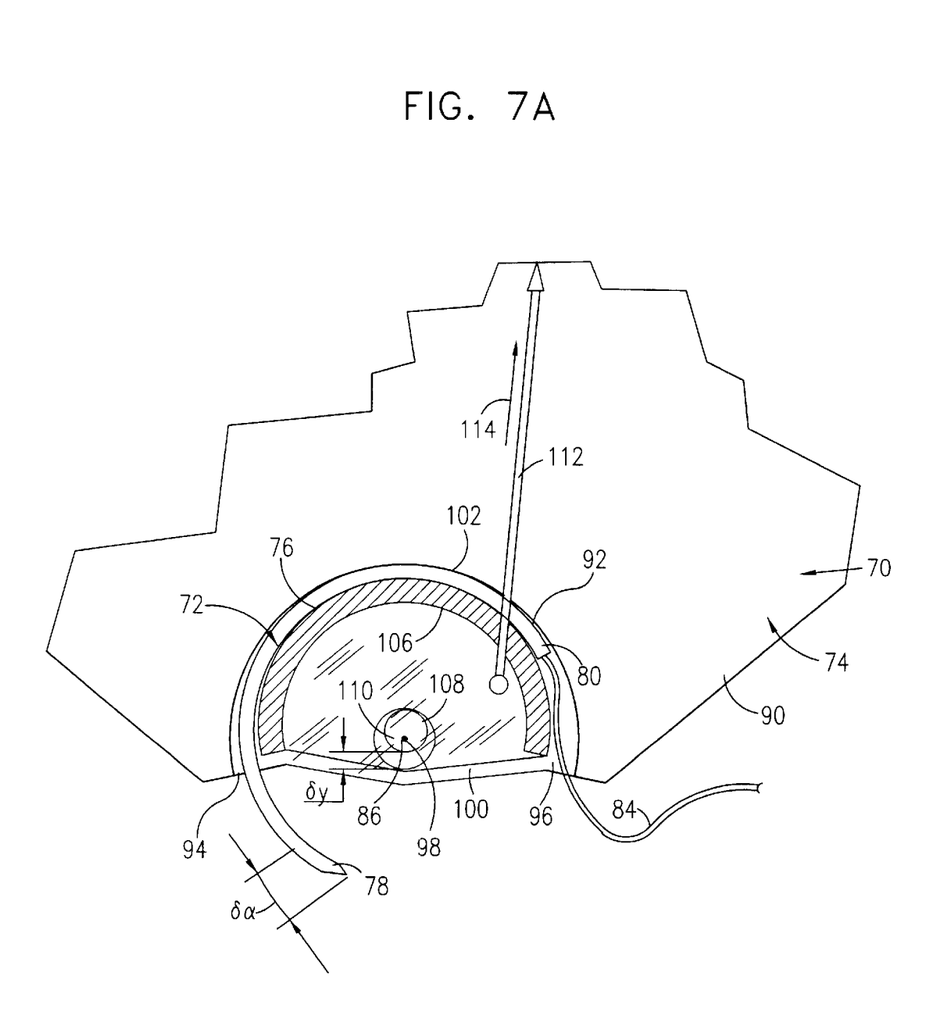
FIGS. 7A is a simplified illustration of angularly advancing a needle through a channel of the stitching tool of FIG. 5 in accordance with a preferred embodiment of the present invention.
Figure 7B:
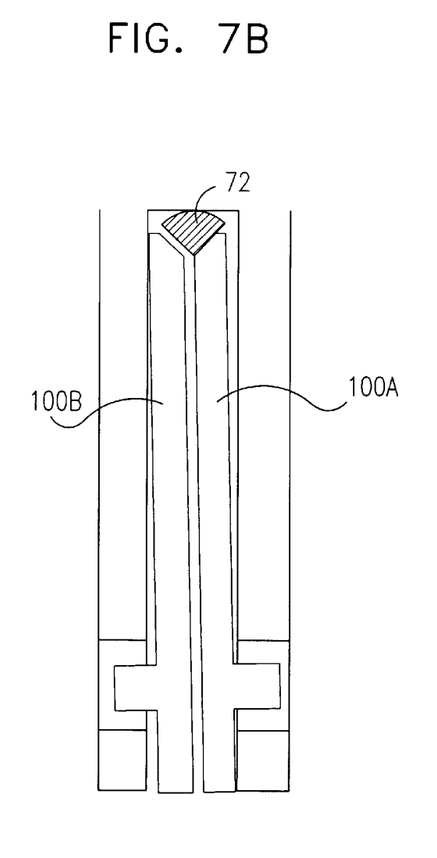
FIG. 7B is a side view illustration of pulling a link to advance the needle through the channel corresponding to FIG. 7A.
Figure 7C:
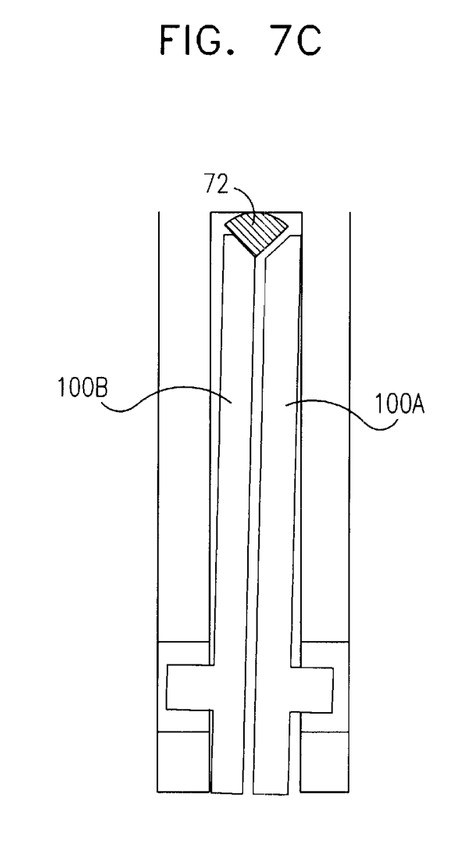
FIG. 7C is a side view illustration of pushing the link of FIG. 7B to prevent regressive movement of the needle opposite to the advanced movement.

Reference is now made to FIGS. 7A–7C which illustrate operation of stitching tool 70 in accordance with a preferred embodiment of the present invention. In FIG. 7A, link 112 is pulled in the direction of arrow 114 and forces disc half 100A to move a distance δy, thereby pinching needle 72 between disc half 100A and low friction upper housing portion 102. The distance δy is basically the clearance between axle 100 and hole 108. Continued pulling of link 112 in the direction of arrow 114 causes disc half 100A not only to translate δy, but also to rotate an angle δα, due to the eccentric mounting of fink 112 to disc half 100A, thereby advancing needle point 78 the same angle δα. As described hereinabove, the high friction contact between needle 72 and rim 106 permits link 112 to impart motion to needle 72 and the low friction contact of needle 72 with upper housing portion 102 allows needle 72 to move through channel 92.

In FIG. 7B, it is seen that when link 112 is pulled in the direction of arrow 114, disc half 100B does not contact needle 72. Thus, when needle 72 is advanced angle δα, disc half 100B does not touch needle 72.

In between incremental pulling of link 112 in the direction of arrow 114, link 112 is pushed in the direction of arrow 115. This orientation is shown in FIG. 7C. It is seen that disc half 100B now presses needle 72 against upper housing portion 102, thereby preventing needle 72 from regressing in channel 92 between pulls of link 112.

Repeated movement of link 112 in the direction of arrow 114 incrementally rotates needle 72 about focus 86. Knots are then tied as described hereinabove with reference to stitching tool 10.

Figure 8:
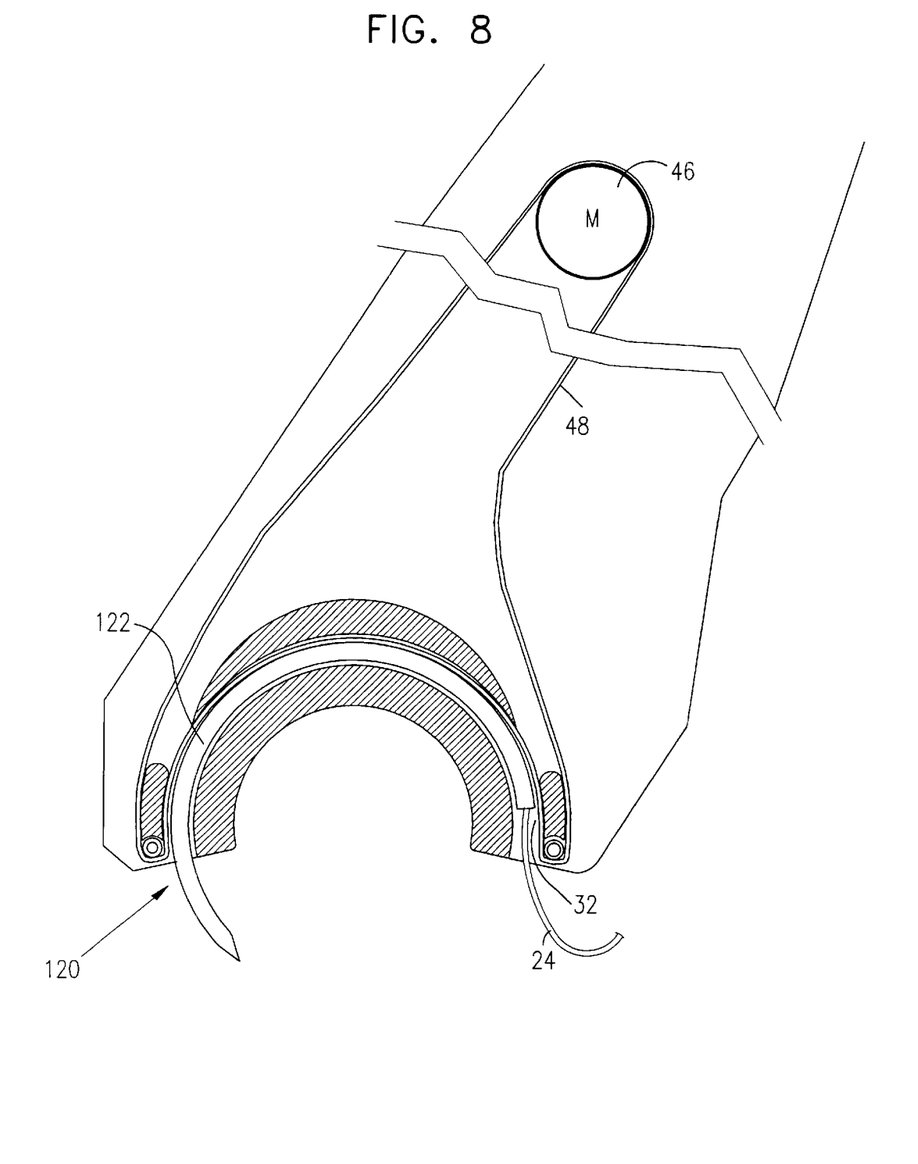
FIG. 8 is a simplified pictorial illustration of a stitching tool constructed and operative in accordance with yet another preferred embodiment of the present invention.

Reference is now made to FIG. 8 which illustrates a stitching tool 120 constructed and operative in accordance with yet another preferred embodiment of the present invention. Stitching tool 120 is preferably substantially similar to stitching tool 10 described hereinabove with reference to FIG. 1, with like elements referenced by like numerals. Stitching tool 120 differs from stitching tool 10 in that instead of the needle being toothed, a standard, smooth arcuate needle 122 is employed. Actuator 46 moves needle 122 by means of belt 48 snugly fit between needle 122 and arcuate channel 32. The surface of belt 48 which contacts needle 122 has a higher coefficient of friction than the surface of belt 48 which contacts arcuate channel 32. Belt 48 presses against needle 122 and as actuator 46 moves belt 48, belt 48 moves needle 122 by means of friction through channel 32.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill.

What is claimed is:

1. A stitching tool comprising:
   a needle comprising an arcuate shank having an arcuate length extending from a needle point at one end thereof to another end, called a suture end, said arcuate shank defining a curve having at least one shank focus; and
   a needle manipulator comprising a housing with an arcuate channel formed therein through which moves said needle, said channel defining an arc extending from a first end to a second end having at least one channel focus, wherein as said needle moves through said channel, said needle point exits said housing at said first end and re-enters said housing at said second end and said arc is sufficiently long such that at least one of said needle point and said suture end is always in said channel during moving of said needle;

wherein said arcuate channel is bounded by a disc, which rotates about said at least one shank focus, and an upper housing portion, and said disc comprises an axle disposed in an enlarged hole so that said axle is translatable within said enlarged hole, and said disc is rotatable eccentrically about said at least one shank focus.

2. The stitching tool according to claim 1 wherein said disc comprises a rim with a surface that is contactable with said needle and said upper housing portion comprises a surface that is contactable with said needle, wherein the contactable surface of said rim has a higher frictional contact with said needle than the contactable surface of said upper housing portion.

3. The stitching tool according to claim 1 further comprising a link eccentrically attached to said disc, wherein pulling of said link in a direction away from a centerline of said disc pinches said needle between said disc and said upper housing portion and further pulling of said link causes said disc and said needle to rotate about said at least one shank focus.

4. The stitching tool according to claim 1 wherein said disc comprises a first half and a second half, and a link is attached to said first half, wherein pulling of said link in a direction away form a centerline of said disc causes said first half of said disc to pinch said needle between said disc and said upper housing portion and further pulling of said link causes said first half of said disc and said needle to rotate an advancing angular movement about said at least one shank focus, and pushing said link in a direction towards said centerline causes said second half of said disc to press agent said needle and to prevent regressive angular movement of said needle opposite to said advancing angular movement.

* * * * *